United States Patent
Ishida et al.

(10) Patent No.: US 8,542,249 B2
(45) Date of Patent: Sep. 24, 2013

(54) MEDICAL IMAGE DISPLAY APPARATUS AND METHOD, AND PROGRAM FOR DISPLAYING MEDICAL IMAGE

(75) Inventors: Hironobu Ishida, Kanagawa (JP); Masashi Murayama, Kanagawa (JP); Keiji Sugihara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1093 days.

(21) Appl. No.: 12/458,879

(22) Filed: Jul. 27, 2009

(65) Prior Publication Data

US 2010/0053213 A1    Mar. 4, 2010

(30) Foreign Application Priority Data

Sep. 1, 2008 (JP) ................... 2008-223081

(51) Int. Cl.
*G09G 5/00*     (2006.01)

(52) U.S. Cl.
USPC ........... 345/629; 345/581; 345/619; 345/660; 345/684

(58) Field of Classification Search
None
See application file for complete search history.

(56) References Cited

U.S. PATENT DOCUMENTS

| | | | |
|---|---|---|---|
| 2002/0099273 A1* | 7/2002 | Bocionek et al. | 600/300 |
| 2004/0151358 A1* | 8/2004 | Yanagita et al. | 382/132 |
| 2008/0183069 A1* | 7/2008 | Fujimoto | 600/411 |

FOREIGN PATENT DOCUMENTS

| | | |
|---|---|---|
| JP | 2002-034948 A | 2/2002 |
| JP | 2003-180684 A | 7/2003 |
| JP | 2007-185215 | 7/2007 |
| JP | 2008-006169 | 1/2008 |

* cited by examiner

*Primary Examiner* — Kee M Tung
*Assistant Examiner* — Jwalant Amin
(74) *Attorney, Agent, or Firm* — Jean C. Edwards, Esq.; Edwards Neils PLLC

(57) ABSTRACT

A storage device of a report producing terminal stores an importance table. The importance table stores grades of importance of respective items of accessory information on medical images. Prior to displaying a medical image on a screen, an area defining section extracts a main subject display area of the medical image, and defines an accessory information display area outside the main subject display area. A display style defining section calculates a necessary display area for each individual item of the accessory information, and discriminates between those items which fit in the accessory information display area and those which do not. The display style defining section decides not to display the items which do not fit in the accessory information display area, or decides to display them in a transparent style, in a scrolling style, in a switching style or with a small font.

22 Claims, 13 Drawing Sheets

F I G. 5

| ITEM | CONTENT | NECESSARY AREA | |
|---|---|---|---|
| | | WIDTH | HEIGHT |
| DATE OF INSPECTION | JULY 3, 2008 | W1 | H1 |
| COMMENT | EARLY STAGE STOMACH CANCER... | W2 | H2 |
| NAME OF PATIENT | TARO FUJI | W3 | H3 |
| PATIENT ID | 0123456789 | W4 | H4 |
| SEX / BIRTH DATE | MALE / APRIL 12, 1950... | W5 | H5 |
| ... | ... | ... | ... |

F I G. 6

| ITEM | IMPORTANCE |
|---|---|
| DATE OF INSPECTION | 100 |
| COMMENT | 80 |
| NAME OF PATIENT | 40 |
| PATIENT ID | 15 |
| SEX / BIRTH DATE | 10 |
| ... | ... |

```
DATE OF INSPECTION: JULY 3, 2008
COMMENT: EARLY STAGE STOMACH CANCER, LIPEMIA;
NEED TO CHECK UP ON ANY METASTASIS
NAME OF PATIENT: TARO FUJI
```
62, 82

FIG. 11B

```
DATE OF INSPECTION: JULY 3, 2008
COMMENT: EARLY STAGE STOMACH CANCER, LIPEMIA;
NEED TO CHECK UP ON ANY METASTASIS
PATIENT ID: 0123456789
```
62, 82

FIG. 11C

```
DATE OF INSPECTION: JULY 3, 2008
COMMENT: EARLY STAGE STOMACH CANCER, LIPEMIA;
NEED TO CHECK UP ON ANY METASTASIS
SEX: MALE   BIRTH DATE: APRIL 12, 1950
```
62, 82

F I G . 12

DATE OF INSPECTION: JULY 3, 2008
COMMENT: EARLY STAGE STOMACH CANCER, LIPEMIA;
NEED TO CHECK UP ON ANY METASTASIS

NAME OF PATIENT: TARO FUJI
PATIENT ID: 0123456789
SEX: MALE, BIRTH DATE: APRIL 12, 1950

MEDICAL IMAGE DISPLAY APPARATUS AND METHOD, AND PROGRAM FOR DISPLAYING MEDICAL IMAGE

CROSS-REFERENCE TO RELATED APPLICATIONS

The present application claims priority from Japanese Patent Application No. 2008-223081, filed Sep. 1, 2008, the contents of which are herein incorporated by reference in their entirety.

FIELD OF THE INVENTION

The present invention relates to a medical image display apparatus and a medical image display method, and a program for displaying a medical image, which permit displaying a medical image and its accessory information overlapped with each other on a screen of a display device.

BACKGROUND OF THE INVENTION

Medical practices have recently been introducing various computer systems that deal with medical documents such as medical reports, hereinafter called simply as the reports, in the form of electronic data to facilitate making and managing the medical documents. Among those computer systems for medical use, a report maker assistant system that facilitates making the report is widely used in practice.

The report maker assistant system is constituted of a report producing terminal, and a database server storing data of the reports produced on the report producing terminal. In addition to the report data, the database server stores data of medical images, which are taken by medical inspection equipments or modalities such as CR (Computed Radiography), CT (Computed Tomography), and MRI (Magnetic Resonance Imaging).

The report producing terminal is operated, for instance, by a doctor who is specialized in diagnosis based on the medical images, hereinafter referred to as an interpreting doctor. The report producing terminal accepts entry of a finding, that is, an observation record about the condition of a lesion perceived by the interpreting doctor in the medical image. The report producing terminal has an editorial function of compiling data of the entered findings into a report. The interpreting doctor makes the report while observing the medical images on a display device of the report producing terminal or a specific display device.

The database server stores the data of the reports and the medical images so as the data to be readable through a network. A doctor who requests a radiological image interpretation, hereinafter referred to as the requesting doctor, makes an access to the database server through a terminal installed in a diagnosis-and-treatment department, to retrieve and view the report data and the medical image data.

The medical image is accompanied with various accessory information like patient ID, patient's name, sex and birth date of patient, inspection ID, date of inspection or image-capturing, conditions of the image-capturing, and the kind of inspection. As indexes for making the report, the accessory information and the medical image are displayed on the same display screen.

JPA 2007-185215 discloses a medical image display apparatus that specifies several display modes for the medical image and its accessory information. For example, the largest site is identified among those sites of a test body which are contained in tomograms, and an area of the largest site is determined in each image, so that the accessory information may not overlap the determined image area on the display screen. In a first embodiment of this prior art, that may be called "text-priority image-shift mode", or a second embodiment called "image-priority text display mode", either the image or the accessory information is shifted so as to avoid the overlap of the accessory information with the determined image area on the screen.

In a third embodiment of the prior art, called "region of interest preset mode", the interpreting doctor designates a region of interest (ROI) in the medical image on the screen, so that the displayed accessory information may not overlap with the designated region of interest. The prior art also discloses another embodiment called "image reduction mode", wherein the size of the medical image is reduced on the screen depending upon the volume of the accessory information to be displayed together, so as to avoid the overlap of the accessory information with the medical image.

Being essential data for the diagnosis, the medical image is expected to be displayed as fine and clear as possible. On the other hand, the accessory information includes requisite data items necessary for radiological interpretation and report-making and non-requisite data items. The value of each data item of the accessory information may vary with the requesting doctor, the interpreting doctor or the patient under the inspection. For these reasons, it is preferable to attach higher priority to displaying valuable data items and give lesser priority to unimportant data items.

According to the first and second embodiments of the above mentioned prior art, one of the display sections for the medical image and the accessory information is shifted while the other is fixed. Because the respective display sections cannot move beyond the display screen, there is a certain limit to the shift amount of the display section. It means that the respective display sections may sometimes overlap. In the overlapped part, visibility of the medical image or the accessory information gets worse. This may lead to medical errors such as a misdiagnosis and the oversight of a lesion. Beside that, the shifted display section of the medical image or the accessory information from its normal position makes it difficult to compare the medical image with past medical images.

The third embodiment of the prior art requires the interpreting doctor to designate the region of interest, which is inconvenient and troublesome. The fourth embodiment is expected to be applied to those medical images which are pasted on such a report that does not require detailed image-interpretation, wherein image deterioration through the size reduction is no problem. Concerning the medical image to be subjected to the radiological interpretation, however, the size reduction causes the problem that the image deterioration decreases the accuracy of the diagnosis.

SUMMARY OF THE INVENTION

In view of the foregoing, a primary object of the present invention is to provide an apparatus, a method or a program, which permit displaying the accessory information effectively with the medical image on the same screen without damaging the visibility of the medical image.

A medical image display apparatus of the present invention comprises a display controller for displaying a medical image and appendant information about the medical image overlapped with each other on a display screen, the appendant information consisting of a plurality of items; a storage device for storing respective grades of importance attached to the appendant information items; and a display style deciding device for deciding how to display the appendant information in an appendant information display area that is provided outside a main subject display area of the medical image, wherein the display style deciding device decides priority in arranging the appendant information items in the order of most important first.

Preferably, the medical image display apparatus further comprises an area defining device that analyzes the medical image to extract the main subject display area, and defines the appendant information display area outside the extracted main subject display area.

The display style deciding device preferably compares the size of a necessary area for displaying the appendant information items in a regular style with the size of the appendant information display area, to discriminate between those appendant information items which fit in the appendant information display area and those which do not fit in the appendant information display area.

According to an embodiment, the display style deciding device decides not to display those appendant information items in the appendant information display area, which do not fit in the appendant information display area.

According to another embodiment, the display style deciding device sets up a transparent display frame in the main subject display area, the transparent display frame displaying those appendant information items which do not fit in the appendant information display area, transparently at a lower density than a regular display density in the appendant information display area.

Preferably, the display style deciding device compares the grade of importance of each of those appendant information items which do not fit in the appendant information display area with a predetermined threshold value, to discriminate between those appendant information items which are to be displayed in the transparent display frame and those which are not to be displayed in the transparent display frame.

Alternatively, the display controller changes transparency of the transparent display frame according to the grade of importance of the appendant information item displayed therein.

According to another preferred embodiment, the display style deciding device sets up a regular display frame for displaying the appendant information in the regular style and an irregular display frame for displaying the appendant information in an irregular style different from the regular style within the appendant information display area. In this embodiment, the display style deciding device decides to arrange those appendant information items which are given higher grades of importance preferentially in the regular display frame.

The display style deciding device may decide all of those information items which cannot be displayed in the regular display frame to be displayed in the irregular display frame. Alternatively, the display style deciding device compares the grade of importance of each of those appendant information items which cannot be displayed in the regular display frame with a predetermined threshold value, to discriminate between those appendant information items which are to be displayed in the irregular display frame and those which are not to be displayed in the irregular display frame.

The regular display frame may be for displaying the appendant information constantly as a whole in a regular size. On the other hand, the irregular display frame may include a scroll display frame for displaying the appendant information item in a scrolling fashion, a switching display frame for displaying a plurality of the appendant information items by turns, or a small font display frame for displaying the appendant information item with a smaller font size than a font size in the regular display frame.

Preferably, the display controller changes the speed of scrolling, the speed of switching, or the font size of the appendant information item in accordance with the importance of each individual appendant information item displayed in the irregular display frame.

According to another preferred embodiment, the appendant information display area includes a first display area for displaying those appendant information items which are previously attached to the medical image before being displayed on the display screen, and a second display area for displaying such appendant information that is attached to the medical image after being displayed on the display screen, such as an annotation to a region of interest of the medical image. In this embodiment, the display controller treats the first and second display areas as separate layers, such that one of the first and second display areas is set to be an upper layer and superposed on the other display area of a lower layer so as to hide the display area of the lower layer behind the display area of the upper layer, or such that only one of the first and second display areas is displayed on the display screen, while the other display area is not displayed.

Preferably, the display style deciding device decides whether or not to display an appendant information item that will overlap with a region of the medical image by comparing importance between the region of the medical image and the appendant information item in question. More preferably, the medical image display apparatus further comprises an importance calculator that analyzes the medical image to grade the importance of respective regions of the medical image.

A medical image display method of the present invention includes a storing step, a display style deciding step and a display control step, so as to display a medical image and appendant information about the medical image overlapped with each other on a display screen of a medical image display apparatus. In the storing step, an importance table grading importance of respective items of the appendant information is stored in a storage device of the medical image display apparatus. In the display style deciding step, a display style of the appendant information is decided, based on the importance table, with use of a display style deciding device of the medical image display apparatus, such that the appendant information items are displayed in the order of most important first. The appendant information is displayed in an appendant information display area that is provided outside a main subject display area of the display screen. In the display control step, the display of the medical image and the appendant information is controlled according to the decided display style, with use of a display controller of the medical image display apparatus.

Preferably, the display style deciding step further includes a step of deciding how to deal with those appendant information items which cannot be displayed in a regular style in the appendant information display area.

A computer-readable medium of the present invention contains a program for controlling a computer to perform a medical image display process for displaying a medical image and appendant information about the medical image overlapped with each other on a display screen of the computer. The medical image display process includes a display style deciding step and a display control step. In the display style deciding step, a display style of the appendant information is decided with use of a display style deciding device of the computer, such that the appendant information items are displayed in the order of most important first. The appendant information is displayed in an appendant information display area that is provided outside a main subject display area of the display screen. In the display control step, the display of the medical image and the appendant information is controlled according to the decided display style, with use of a display controller of the computer.

The present invention permits displaying the accessory information on the medical image effectively without reducing visibility of the medical image, because more important accessory information items are displayed in the regular style that is superior in visibility, while less important accessory information items, which are not displayable in the regular style in the appendant information display area, are omitted from the display screen or displayed as much as possible in a different display style from the regular style, so that the medical image is maintained unchanged.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 5 is an explanatory diagram illustrating an example of stored information on the sizes of necessary display areas for the accessory information items;

FIG. 6 is an explanatory diagram illustrating an example of an importance table;

FIG. 11 is a diagram illustrating an example of an image display screen provided with a switching display frame according to a fourth embodiment of the present invention;

FIG. 12 is a diagram illustrating an example of an image display screen provided with a small font display frame according to a fifth embodiment of the present invention;

FIG. 13 is a diagram illustrating a sixth embodiment of the present invention.

DESCRIPTION OF THE PREFERRED EMBODIMENTS

First Embodiment

Figure 1:
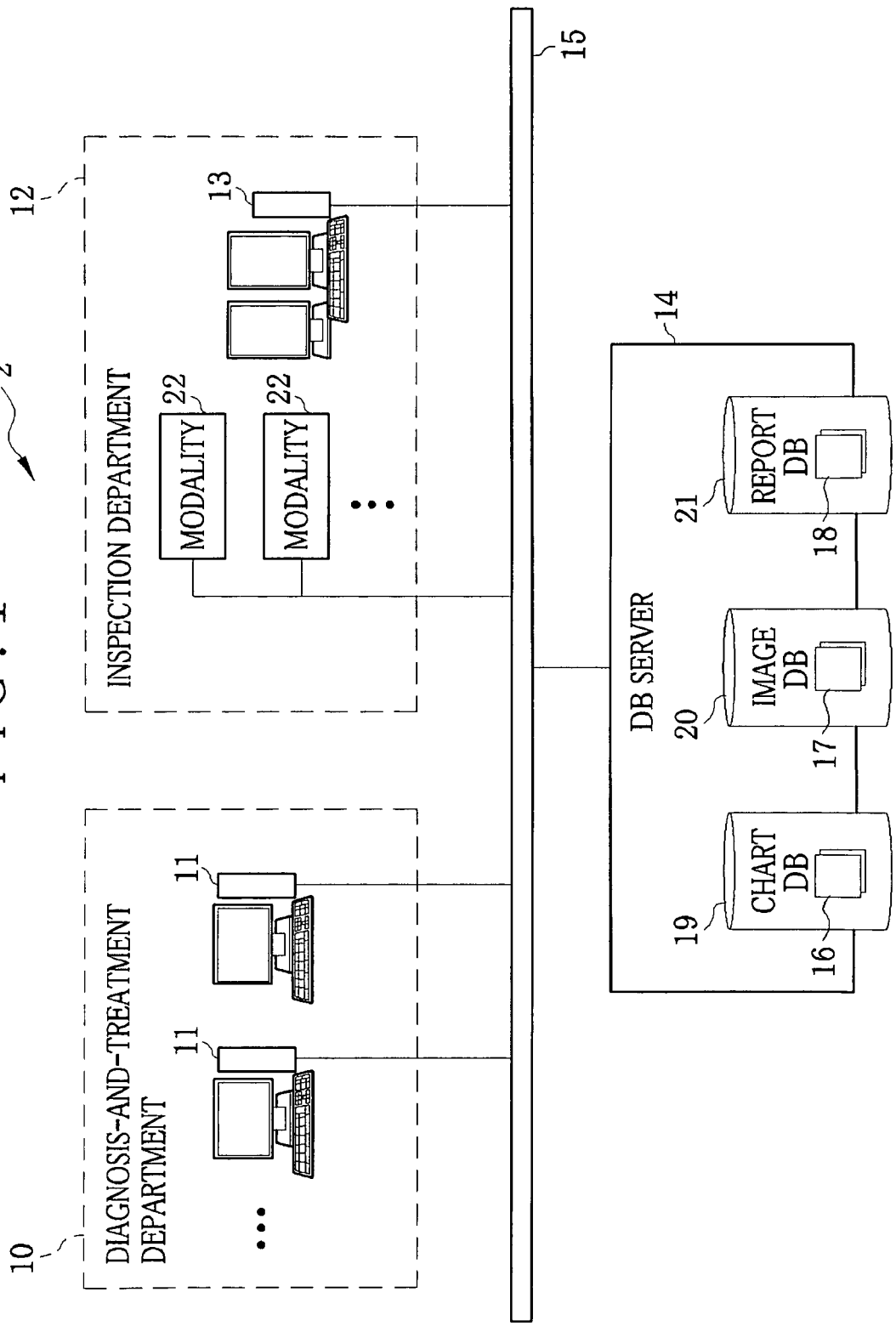
FIG. 1 is a configuration diagram of a medical information system.

In FIG. 1, a medical information system is constructed in a medical facility such as hospital, and comprises diagnosis-and-treatment department terminals 11 arranged in diagnosis-and-treatment departments 10, a report producing terminal 13 arranged in a radiological inspection department, hereinafter called simply as the inspection department 12, and a database (DB) server 14, which are all connected to a network 15 to communicate with each other. The network 15 is for example a LAN (Local Area Network) in a hospital.

The diagnosis-and-treatment department terminals 11 are operated by doctors in the diagnosis-and-treatment departments 10, to browse and input data on patients' records called charts 16 or issue orders for inspections to the inspection department 12. The diagnosis-and-treatment department terminal 11 also displays medical images 17 as obtained through an inspection as well as reports 18 on the result of the inspection, which are submitted from the inspection department 12. The doctor who requested the inspection, hereinafter called the requesting doctor, reads the report with the medical image on the diagnosis-and-treatment department terminal 11.

The report producing terminal 13 is operated by a doctor of the inspection department 12, who is specialized in radiological image interpretation, hereinafter called the interpreting doctor. The interpreting doctor uses the report producing terminal 13 for checking the orders from the requesting doctors and making the reports 18. The report producing terminal 13 assists the interpreting doctor to make the report 18 by displaying an image display screen 46 and a report editor screen 47 (see FIG. 3).

In the DB server 14 are built up a plurality of databases, including a chart database 19, an image database 20 and a report database 21. The chart database 19 stores data of every patient's medical chart 16, the image database 20 stores data of medical images 17 taken by medical inspection equipments or modalities 22 such as CR devices, CT scanners and MRI machines. The report database 21 stores the data of reports 18 produced on the report producing terminal 13.

The DB server 14 receives via the network 15 the data of the medical images 17 taken by the modalities 19 and stores the data in the image database 20. The DB server 14 functions as a PACS (Picture Archiving and Communication Systems) server; the DB server 14 and the modalities 19 constitute the Picture Archiving and Communication System.

The medical image 17 is given an individual image ID for identification. The data of each medical image 17 is stored as a file that complies, for example, with the DICOM (Digital Imaging and Communication in Medicine) format, where a DICOM tag is attached to each file. The DICOM tag records accessory information, or appendant information, such as patient ID, name, sex and birth date of patient, inspection ID, date of inspection (date of imaging), imaging condition, and kind of inspection. So the data files of the medical images 17 are retrievable from the image database 20 by designating an information item in the DICOM tag as a search key.

The DB server 14 constitutes a medical chart system in cooperation with the diagnosis-and-treatment department terminals 11 and the chart database 19. The database server 14 also constitutes a report making assisting system in cooperation with the report producing terminal 13, the image database 20 and the report database 21. Like the data of the medical images 17, the data of the reports 18 stored in the report database 21 is retrievable with a search key such as the inspection ID, the patient ID and the name of patient. Although the respective databases 19 to 21 are built up in the same DB server 14 in the present embodiment, it is possible to build up the databases 19 to 21 separately in different database servers.

An order issued from the diagnosis-and-treatment department terminal 11 includes several items of information, including a patient ID, a patient's name, a request date, a requester, an inspection kind, like CT or MRI, inspection purposes, need for radiological interpretation, and comments of the requesting doctor, like a message to the interpreting doctor. Some of these items, like the requester and the comments, are also dealt with as the accessory information on the medical image. As the items of the requester is recorded information on the requesting doctor, such as its department, e.g. internal medicine or brain surgery, its name, and its doctor ID. The inspection purposes may for example be a judgment about therapeutic effect on a lesion under the therapy and a result of a search for a metastasis.

The order issued from the diagnosis-and-treatment department terminal 11 is sent to and received on an order receiving terminal that is not shown in the drawings but installed in the inspection department 12. The order receiving terminal gives an inspection ID to the received order and manages the data of the orders. The inspection ID is sent with an acknowledgment to the diagnosis-and-treatment department terminal 11. The staff of the inspection department 12, a radiologist, takes medical images by the modality 22 according to the order received on the order receiving terminal.

When the radiological interpretation is requested in the item of the need for the radiological interpretation in the order, the order is sent with the given inspection ID from the order receiving terminal to the report producing terminal 13. An interpreting doctor checks the order at the report producing terminal 13, and reads the data of those medical images 17 which are to be subjected to the radiological interpretation out of the image database 20. The interpreting doctor puts the result of interpretation of the medical images 17 into the report 18.

After completing the report 18, the interpreting doctor sends a notice of report completion from the report producing terminal 13 to the diagnosis-and-treatment department terminal 11 of the requester. The notice of report completion includes respective addresses in the databases 20 and 21 where the data of the interpreted medical images 17 and the report 18 of the interpretation are stored respectively. The requesting doctor gets the addresses from the notice of report completion, and makes an access to the addresses through the diagnosis-and-treatment department terminal 11, to retrieve and browse the medical images 17 and the report 18.

The respective terminals 11 and 13 and the DB server 14 are configured based on computers such as a personal computer, a server computer or a workstation, by installing the computers with control programs such as one for an operating system and application programs such as client programs or server programs.

Figure 2:
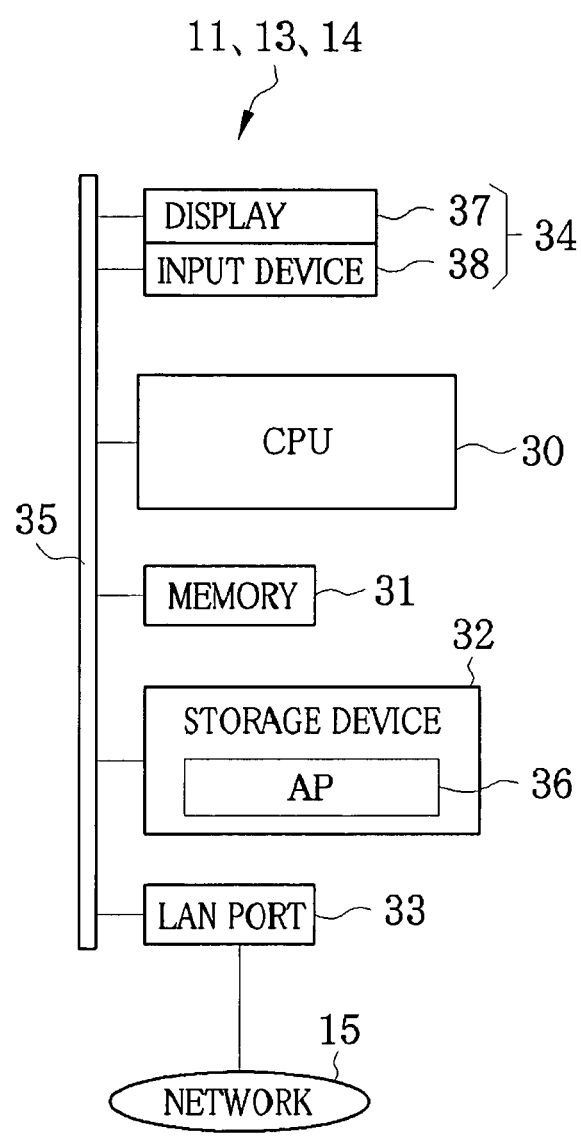
FIG. 2 is a configuration diagram of a computer, based on which a department terminal, a report producing terminal and a database server is individually configured.

As shown in FIG. 2, the computers for the DB server 14 and the respective terminals 11 and 13 have the same basic structure, and are provided with a CPU 30, a memory 31, a storage device 32, a LAN port 33 and a console 34, all of which are connected to each other via a data bus 35.

The storage device 32 is, for example, a Hard Disk Drive (HDD) and stores the control program and the application program, hereinafter referred to as AP 36. The storage device 32 of the report producing terminal 13 further stores an importance table 70 (see FIG. 6) that shows the grades of importance of the respective items of the accessory information attached to the medical image 17.

The database server 14 is provided with a disk array consisting of plural apposed HDDs as another storage device 32 for the database besides the HDD that stores the programs. The disk array can be built in a server body or arranged outside the server body and connected to the server body via a cable or a network.

The memory 31 is a work memory for the CPU 30 to carry out its processes. The CPU 30 controls the overall operation of every part of the computer, downloading the control program from the storage device 32 onto the memory 31 and performing the processes according to the control program.

The LAN port 33 is a network interface controlling transmission with the network 15. The console 34 consists of a display device 37 and an input device 38 like a keyboard, a mouse, and a microphone.

The diagnosis-and-treatment department terminal 11 is installed with the client program as the application program 36, such as software for reading or editing the chart 16 and viewer-software for displaying the medical images 17 and the report 18. With the client program running, an operation screen is displayed by a Graphical User Interface (GUI) on the display device 37 of the diagnosis-and-treatment department terminal 11. The operation screen includes display screens for displaying the chart 16, the medical images 17 and the report 18, which are read from the chart database 19, the image database 20 and the report database 21 respectively.

Operation commands are input to the diagnosis-and-treatment department terminal 11 through the input device 38, to input or edit the chart 16 or to input or issue the order. Data of the input chart 16 and data of the input order are stored in the chart database 19.

The report producing terminal 13 is installed with the client program for report-editing as the application program 36. With the client program for report-editing, the report producing terminal 13 executes a display process of the medical images 17 and an edit process of the report 18, to assist the client in making the report 18.

The DB server 14 is installed with the server program as the application program 36. The server program is for executing some processes according to the requests of the clients sent from the respective terminals 11 and 13 and for sending back the result of the process.

Figure 3:
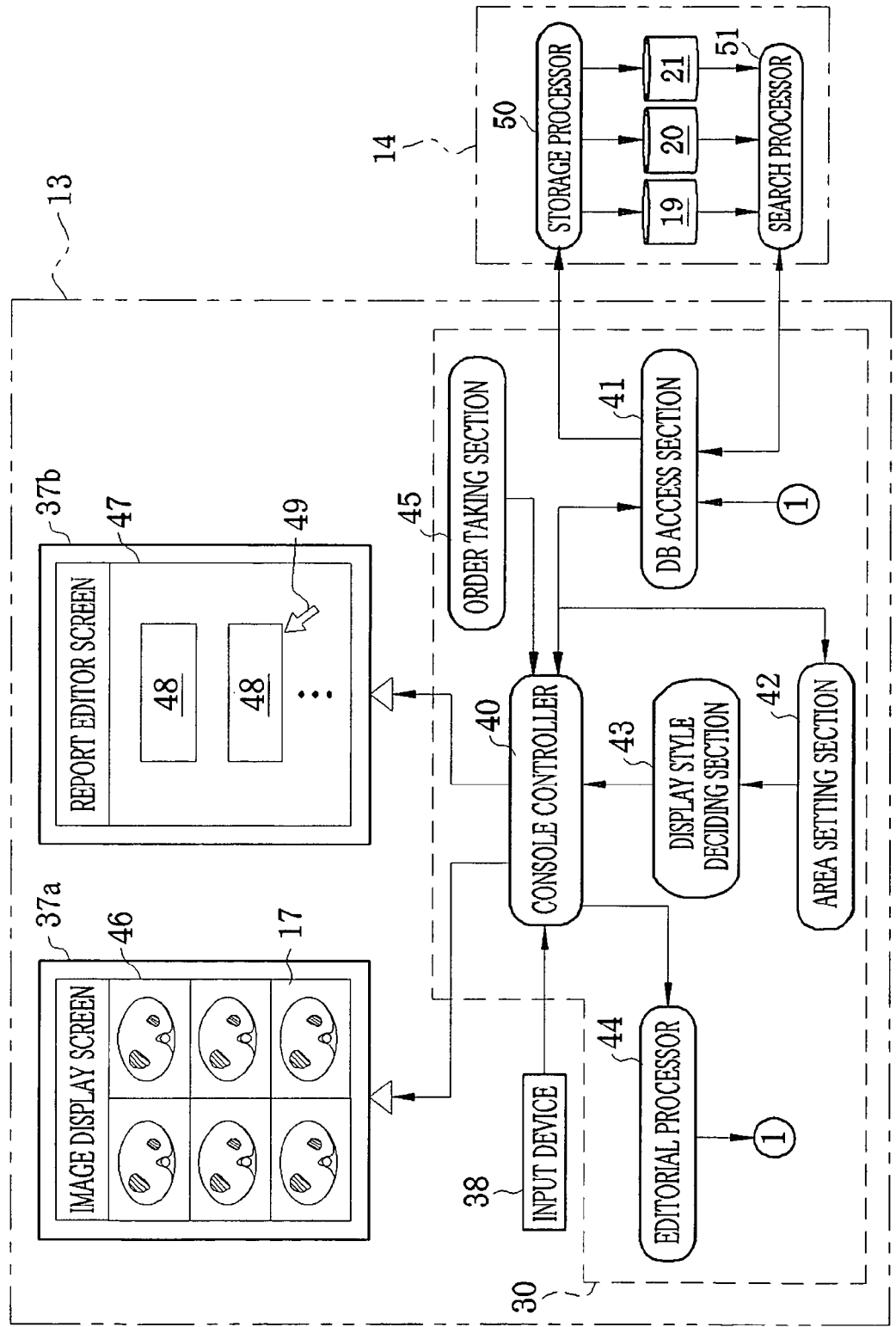
FIG. 3 is a diagram illustrating schematic configurations of the report producing terminal and the database server.

As shown in FIG. 3, while the client program for report-editing is running, the CPU 30 of the report producing terminal 13 functions as a console controller 40, a DB access section 41, an area defining section 42, a display style deciding section 43, an editorial process section 44, and an order taking section 45.

The report producing terminal 13 is a multi-display terminal, wherein two display devices 37a and 37b are connected to a terminal main body, in which the CPU 30 is mounted. An image display screen 46 used for displaying the medical images 17 is displayed on the display device 37a. On the other display device 37b, a report editor screen 47 and report display screens 61 and 66 (see FIGS. 7 and 10) are displayed.

The image display screen 46 and the report editor screen 47 constitute the operation screens of the GUI. The console controller 40 outputs the operation screens onto the respective display devices 37a and 37b, and receives the operation commands from the input device 38 through the operation screens.

The image display screen 46 and the report editor screen 47 get active in cooperation with each other. For example, when an inspection ID is input on the report editor screen 47, which includes the medical images 17 as the subject of the radiological interpretation, the console controller 13a obtains the data of the medical images 17 corresponding to the input inspection ID from the image database 20 through the DB access section 41, and activates the image display screen 46 to output the obtained medical images 17 on the display device 37a.

The image display screen 46 displays a variety of medical images 17 such as radiologic perspective images taken by the CR device, tomograms taken by the CT scanner or the MRI machine, or three-dimensional images generated based on the tomograms. The image display screen 46 can display a plurality of the medical images 17 at the same time, as like, for example, six tomograms arrayed on one screen. The image display screen 46 is provided with various operation tools such as operation buttons, list boxes and icons, all of which constitute the GUI. By means of these operation tools, various operation commands are input by operating the input device 39.

Figure 4:
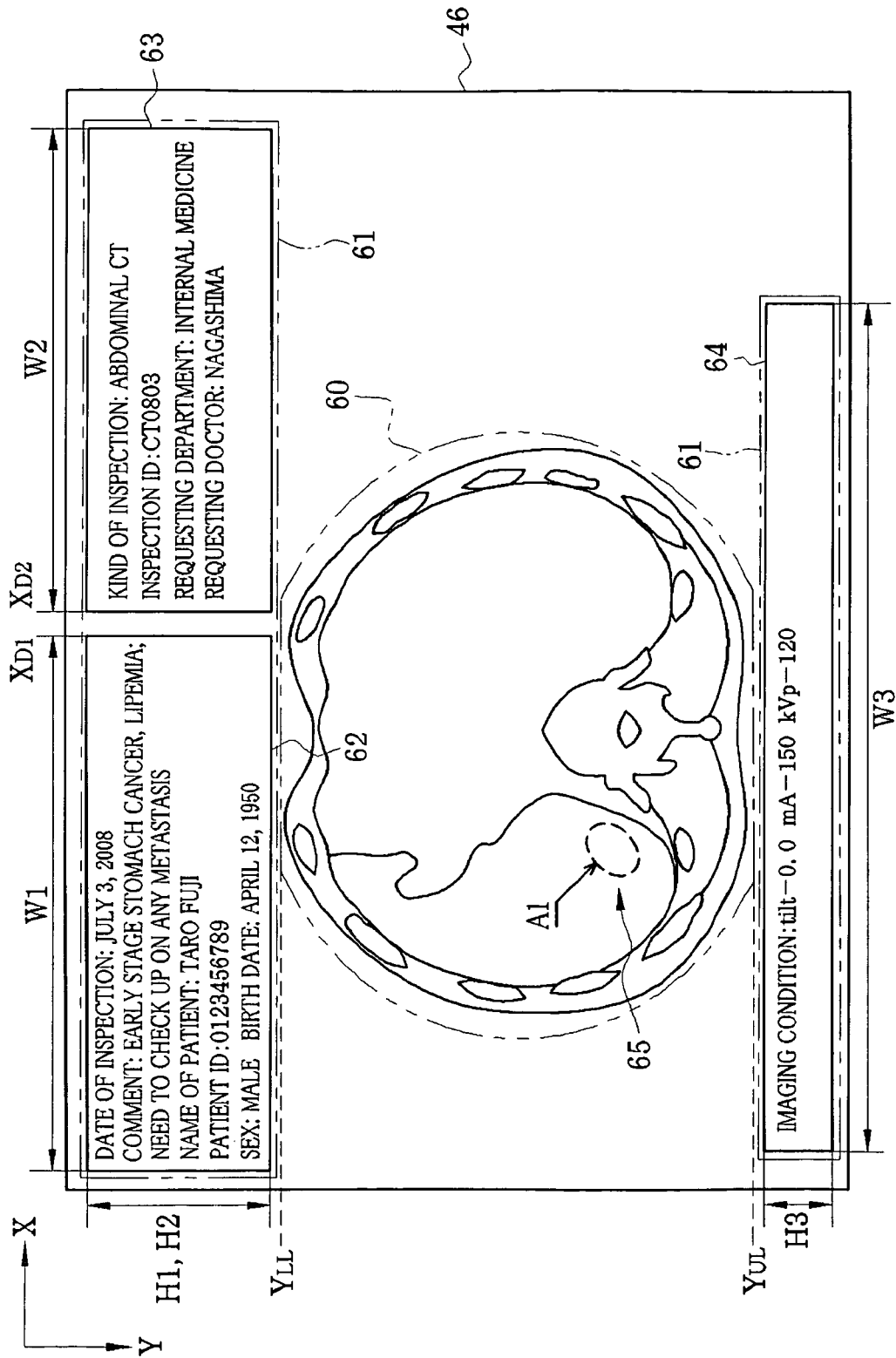
FIG. 4 is an explanatory diagram illustrating an image display screen displaying all data items of accessory information.

FIG. 4 shows the image display screen 46 that displays a tomogram taken by a CT or MRI scanner as an example of the medical image 17. The image display screen 46 is sectioned into a main subject display area 60 and an appendant information display area (hereinafter, accessory information display area) 61. These display areas 60 and 61 are defined by the area defining section 42 in size, position and the like. The display style of the accessory information in the accessory information display area 61 is decided by the display style deciding section 43.

The main subject display area 60 constitutes a main part of a subject taken as the medical image 17, i.e. the main subject, which is an abdominal CT tomogram in the illustrated example. The main subject display area 60 is positioned nearly in the center of the image display screen 46. The accessory information display area 61 lists the accessory information about the medical image 17, and is positioned on either vertical side of the main subject display area 60.

The accessory information display area 61 is divided into three sections 62, 63 and 64, the first and second sections 62 and 63 being located at upper left and right positions of the screen 46, and the third section 64 on lower side of the main subject display area 60. Among the items of the accessory information, the first section 62 displays "date of inspection", "comment", "name of patient", "patient ID", and "sex and birth date of patient". The second section 63 displays "kind of inspection", "inspection ID", "requester department", and "requesting doctor". The third section 64 displays "imaging condition". Note that the layout of these display sections 62 to 64 as well as the items displayed therein should not be limited to the present example but may be modified appropriately. For example, the third section 64 may be omitted, or the first and second sections 62 and 63 may be united into an elongated section.

On the image display screen 46, it is possible to add an annotation 65 to the medical image 17 as a process of making the report 18. The annotation 65 means a remark assigned to a region of interest (RIO) like a lesion, which attracts an interest of the interpreting doctor within the medical image 17. The annotation 65 is made of symbols for indicating the region of interest, including an arrow, a circle, characters, and various objects like a text box for writing a short comment therein. The text box may be a rectangular box or a balloon. The annotation 65 may be made of some symbols alone or a text box alone.

Referring back to FIG. 3, the report editor screen 47 is provided with a plurality of finding entry boxes 48. Although it is not shown in the drawings, the report editor screen 47 is also provided with various operation tools and accessory information display areas like as the image display screen 46. Through the operation tools, various operation commands are input from the input device 38. The operation commands are given for example by clicking the mouse while putting a pointer 49 on the appropriate operation tool. The operation commands include a command to read out the data of the report 18 from the report database 21, a command to store the data of the report 18 in the report database 21, and a command to chose and make one of the finding entry boxes 48 active.

The active finding entry box 48 permits writing a text describing a finding, that is, an observation about a lesion or the like, which the interpreting doctor has perceived in the medical image 17 on the image display screen 46. The several finding entry boxes 48 are used to input respective findings on different lesions, or findings for different inspection purposes, e.g. a judgment about therapeutic effect and a result of a search for a metastasis. It is also possible to use the different finding entry boxes 48 for inputting respective findings of different doctors: a trainee doctor and a trainer doctor, or a first-stage interpreting doctor and a second-stage interpreting doctor.

The text data of each finding written in the individual finding entry box 48 has a finding ID for identifying each individual finding. The finding ID correlates the finding with the medical image 17 and the report 18. The finding ID includes a serial number given to each individual finding entry box 48 in order of entry. For example, "F-N" (N=a natural number of not less than 1) is assigned as the finding ID to the text data of the finding that is written in the $N^{th}$ finding entry box 48.

When a command to store the data of the report 18 is given after the report 18 is made up on the report editor screen 47, the data of the report 18 is stored as fixed one in the report database 21. The fixed report 18 is prohibited from being edited for the sake of protection from illegal revision. It is, of course, possible to store incomplete data of the report 18 temporarily in the report database 21.

The database access section 41 sends a request for a process to the database server 14 and receives a result of the process in response to commands from the console controller 40 or the editorial processor 44. The requests sent to the database server 14 include a search request addressed to the image database 20 to search for medical images 17 using the inspection ID or the image ID as a search key, and a storage request and a search request to the report database 21. The storage request is for storing the data of the produced report in the report database 21. The search request to the report database 21 is for retrieving the data of an incomplete report 18 from the report database 21.

The database access section 41 receives the data of the report 18 from the editorial processor 44 as an answer to the storage request, and sends it to the database server 14. The database access section 41 also receives the data of the medical image 17 from the database server 14 as an answer to the search request, and forwards it to the console controller 40, the area defining section 42 and the display style deciding section 43.

The area defining section 42 binarizes the data of the medical image 17 as received from the database access section 41, to convert the medical image 17 to a black-and-white image. Next, the black-and-white image is subjected to a labeling process. Then a main part of the subject captured as the medical image 17 is distinguished from other parts and extracted. Since the method of extracting the main part of the subject through binarization and labeling is known in the art, the detailed explanation of this method is omitted. If necessary, refer to materials, e.g. "Behavioral Decision of Autonomous Mobile Robot with Vision Sensor" written by Tomomitsu YAMAGUCHI and others, issued as a document No. 231-4 at the 231$^{st}$ workshop of northeast branch of Society of Instrument and Control Engineers (Oct. 31, 2006) or JPA 2007-299210.

Tomograms like the example shown in FIG. 4 are taken by the CT or MRI scanner in a continuous succession, slicing across the body axis of the patient at one inspection. So the area defining section 42 treats the successive tomograms taken at one inspection with the binarization and labeling process, to extract a main part of the subject of each individual image. Then the area defining section 42 determines the largest main part to be the main subject, which is displayed as the main subject display area 60.

After extracting the main subject display area 60, the area defining section 42 defines the accessory information display area 61. Concretely, provided that pixel positions on the image display screen 46 are represented by XY-coordinate values, wherein the origin (0,0) of the XY coordinates is for example at the upper left corner of the image display screen 46, whereas the lower right corner of the image display screen 46 has the maximum values ($X_{MAX}$, $Y_{MAX}$), e.g. ($X_{MAX}$, $Y_{MAX}$)=(1023, 767), the area defining section 42 defines the upper accessory information display area 61, i.e. the first and second sections 62 and 63, to be a rectangle with a diagonal line extending from a point (0+α, 0+β) to a point ($X_{MAX}$-α, $Y_{LL}$-β), wherein $Y_{LL}$ (>0) represents the lowest Y coordinate value of the main subject display area 60. That is, the upper rectangular area 61 has a length of $X_{MAX}$-2α in the X-axis direction and a length of $Y_{LL}$-2β in the Y-axis direction. Hereinafter, length in the X-axis direction will be referred to as width, and length in the Y-axis direction as height. Provided that $Y_{UL}$ (<$Y_{MAX}$) represents the highest Y coordinate value of the main subject display area 60, the area defining section 42 defines the lower accessory information display area 61, i.e. the third section 64, to be a rectangle with a diagonal line extending from a point (0+α, $Y_{UL}$+β) to a point ($X_{MAX}$-α, $Y_{MAX}$-β). That is, the lower rectangular area 61 or the third section 64 has a width $W_3$ of $X_{MAX}$-2α and a height $H_3$ of $Y_{MAX}$-$Y_{UL}$-2β. Moreover, the area defining section 42 decides dividing positions $X_{D1}$ and $X_{D2}$ between the first and second sections 62 and 63 appropriately, for example, according to predetermined values. Thereby, the first section 62 has a width $W_1$ of $X_{D1}$-α and the second section 63 has a width $W_2$ of $X_{MAX}$-$X_{D2}$-α, while the first and second sections 62 and 63 have the same height H1 and H2 of $Y_{LL}$-2β. Note that the values α and β represent clearances between the display areas 60 and 61, which prevent obscuring the border between them. For example, α and β correspond to one pixel.

The size of the main subject display area 60 varies from inspection to inspection because the main subject display area 60 is extracted as only one part of a series of tomograms taken at one inspection. So the upper and lower limits $Y_{UL}$ and $Y_{LL}$ of the Y coordinate values of the main subject display area 60 are variable. Accordingly, the size or height of the accessory information display area 61 also varies from inspection to inspection. The area defining section 42 feeds the console controller 40 and the display style deciding section 43 with information on the size of the respective display areas 60 and 61 (62 to 64), i.e. their XY coordinate values, widths and heights.

The display style deciding section 43 first calculates the size of an area necessary for displaying the respective items of the accessory information as character strings or a text, using a predetermined font metrics, which is layout information for use in displaying character strings in a predetermined font. As being received from the database access section 41 or the order taking section 45, the accessory information includes a fragment of accessory information attached to the order as well as information attached to the medical image 17.

As the necessary display area for the accessory information, the display style deciding section 43 calculates the size for displaying every item of the accessory information in a line without wrapping along the X-axis. Since the contents of the accessory information differ from one inspection to another, the length of each line of the character string and thus the width of the necessary display area for the accessory information vary correspondingly, though the height is determined to have the value defined as above. As shown for example in FIG. 5, the display style deciding section 43 temporarily stores data of the calculated size of the necessary display area in the form of a data table in the memory 31. The data table allocates the width "Wi" and the height "Hi" of the necessary display area to the individual item of the accessory information, wherein i=1, 2, 3 . . . , and i≤m, m being a variable number of items assigned to each section 62, 63 or 64.

The display style deciding section 43 decides the style of display of the accessory information with reference to an importance table 70 shown for example in FIG. 6. The importance table 70 is a data table that shows numerical values representative of degrees of importance of the respective accessory information items as criteria for evaluating the respective information items. The importance of the respective items may for example be graded into 0 to 100 degrees; the higher grade represents the greater importance of the information item. In the present embodiment, the greatest importance is attached to the item "date of inspection", given the grade of 100. Lower grades of importance, 80, 40, 15, 10 etc., are assigned to other items "comment", "name of patient", "patient ID", "sex and birth date of patient" etc., respectively.

The level of importance of each item may be preset at a fixed value, or it may be a value variable by the interpreting doctor or some others. The level of importance may also be set for each individual requesting or interpreting doctor. It is also possible to change the importance degrees automatically according to the kind of lesion or inspection. Although the importance degrees are represented in numerical values, it is possible to classify the importance qualitatively, e.g. high, middle and low.

The display style deciding section 43 compares the width Wi of the necessary display area of each individual information item, which is stored in the memory 31, with the width W1, W2 or W3 of assigned one of the first to third sections 62 to 64. The display style deciding section 43 decides that the item with a width Wi of not more than the width W1, W2 or W3 of the assigned section 62, 63 or 64 can be displayed in the assigned section (Wi≤W1, W2 or W3). On the contrary, the display style deciding section 43 decides not to display the item with a width Wi of more than the width W1, W2 or W3 (Wi>W1, W2 or W3).

Thereafter, the display style deciding section 43 adds the heights Hi of the respective necessary display areas of those items which are determined to be fit in width in the assigned section 62, 63 or 64, seriatim in order of most important to least important, to calculate a sum ΣHi. Each after adding the height Hi of the necessary display area of one item, the display style deciding section 43 compares the added height ΣHi with the height H1, H2 or H3 of the applicable section 62, 63 or 64. The display style deciding section 43 makes this comparison to each section 62, 63 or 64 individually, but the following description will exemplify this process as for a case where all items allotted to the first display section 62 are determined to be displayable with respect to the width.

The display style deciding section 43 first adds the height h1 of the most important item "date of inspection" and the height h2 of the second most important item "comment". Then, the display style deciding section 43 compares the sum ΣH2 (=H1+H2) with the height H1 of the first display section 62. The display style deciding section 43 repeats adding the height Hi and comparing the sum with the height H1 so far as the sum ΣHi is not more than the height H1 (ΣHi≤H1).

When the sum ΣHi gets over the height H1 (ΣHi>H1) of the first section 62 before the height Hi of every item allocated to the first display section 62 has been added up, the display style deciding section 43 stops the calculation and decides not to display the item whose height Hi of the necessary display area has just been added in, and the following items whose heights Hi have not yet been added in. For instance, if the sum ΣHi gets over the height H1 when the height h4 of the item "patient ID" is added in (ΣH4>H1), the display style deciding section 43 decides to display the first three items "date of inspection", "comment" and "name of patient", and not to display the following less important items "patient ID" and "sex and birth date of patient".

On the other hand, if the sum ΣHi is less than or equal to the height H1 after the height h5 of the least important item "sex and birth date of patient" is added in (Σh5≤H1), the display style deciding section 43 decides to display all of the items allocated to the first display section 62. The decision by the display style deciding section 43 on the display style of the accessory information items is output to the console controller 40. The console controller 40 controls how to display the display areas 60 and 61 in accordance with the commands from the area defining section 42 and the display style deciding section 43.

As described so far, the display style deciding section 43 finally decides to display such items that can be put into the assigned display section 62, 63 or 64 with regard to the width and the height as well. Since the height Hi of the necessary display area is added up in order of decreasing importance, those items with higher grades of importance will be displayed with higher probability. On the contrary, the items that the display style deciding section 43 decides not to display in the display sections 62 to 64 can be less important ones.

Figure 7:
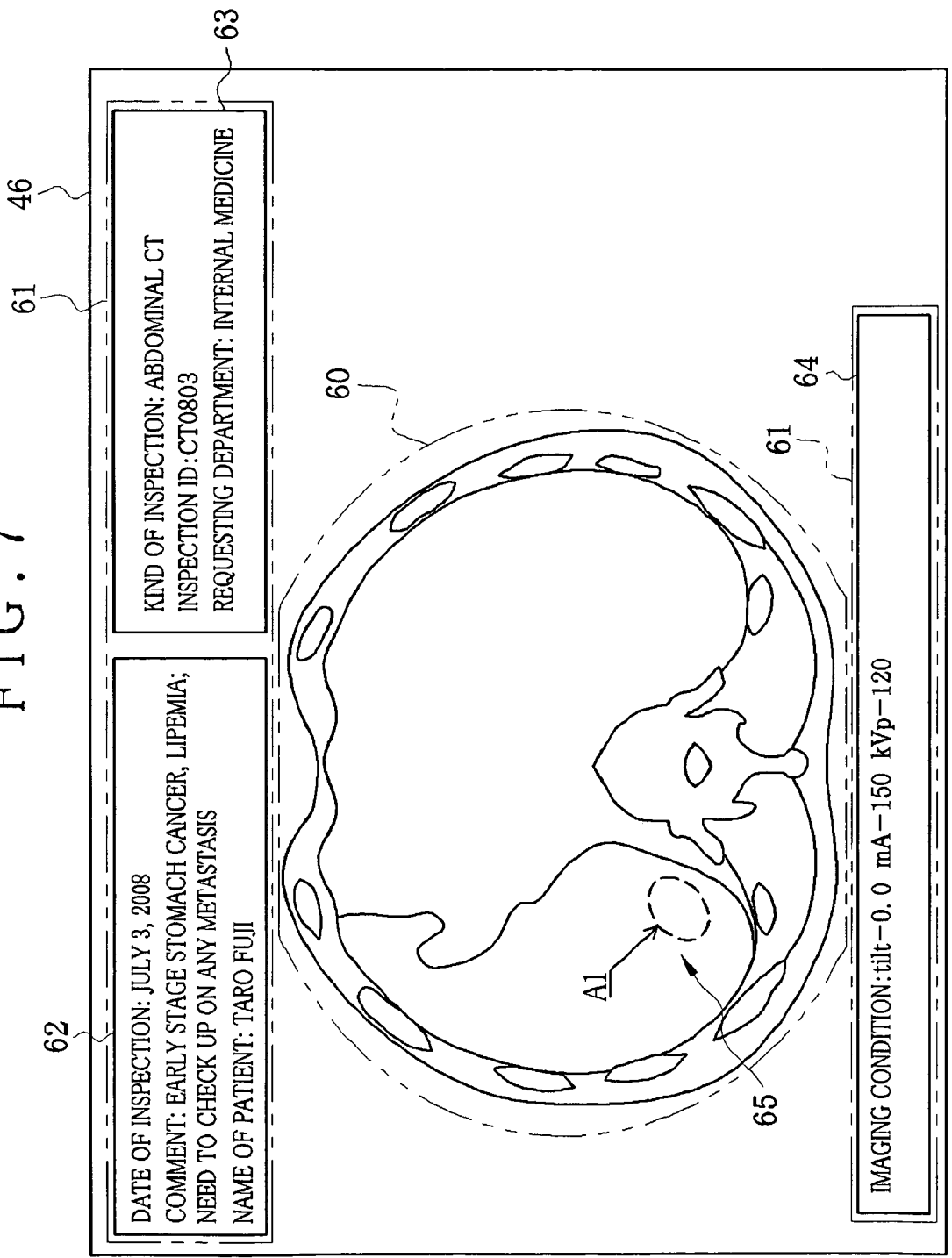
FIG. 7 is a diagram illustrating an example of an image display screen, which displays some of the accessory information items and dose not display others.

FIG. 7 shows a display style on the image display screen 46 according to the decision by the display style deciding section 43 in the above-described example. Namely, the items "date of inspection", "comment", and "name of patient" are displayed in the first section 62, but the less important items "patient ID" and "sex and birth date of patient" are not displayed. In the second section 63, the item "name of requesting doctor" is not displayed in this example. Note that if, for example, the width w2 of the necessary display area for the item "comment" is larger than the width W1 of the first display section 62 (W2>W1), the item "comment" is not displayed, and the item "patient ID" is displayed instead.

In FIG. 3, the console controller 40 accepts an operation command to attend an annotation 65 to the medical image 17 on the image display screen 46 or an operation command to write a finding in one of the finding entry boxes 48 on the report editor screen 47, and instructs the editorial processor 44 to execute a process responsive to the operation command.

Through the console controller 40, the editorial processor 44 accepts data of the finding as written in the finding entry box 48. The editorial processor 44 makes the accepted finding data into a block while discriminating it from one another according to the applied finding entry box 48.

Then the editorial processor 44 attaches an applicable finding ID "F-1", "F-2" or the like, to each block of the finding data, and records the data blocks of the respective findings in the data of the report 18. Besides the finding data, information read out from the order, such as the inspection ID, the patient ID, and the name of patient, are attached by the editorial processor 44 to the data of the report 18. The editorial processor 44 also records the data of the annotation 65, which has been attached to the medical image 17 through the image display screen 46, with the data of the report 18 as well as the medical image 17.

In addition to the finding ID, the editorial processor 44 attaches the doctor ID to each block of the finding data, in order to identify the interpreting doctor who writes the finding in the corresponding finding entry box 48. The doctor ID may for example be input by the individual interpreting doctor as required for user authentication at the activation of the report producing terminal 13. The finding data is thus retrievable with the finding ID and the doctor ID.

The order taking section 45 takes the order from an order reception terminal through the network 15. The order taken by the order taking section 45 is registered in an order table that is not-shown but mounted in the storage device 32 of the report producing terminal 13.

The CPU 30 of the database server 14 executes the server program to work as a storage processor 50 and a search processor 51 for the data of the charts 16, the medical images 17 and the reports 18. The storage processor 50 carries out processes for storing the data in the respective databases 19 to 21 in response to clients' requests for data-storage from the report producing terminals 13 and the modalities 22. The search processor 51 retrieves the data from the databases 19 to 21 and delivers the retrieved data to requesters in response to requests for data-delivery which are sent from the diagnosis-and-treatment department terminals 11 and the report producing terminal 13.

Now the operation of the above-described embodiment will be described with reference to the flowchart shown in FIG. 8. The requesting doctor uses the diagnosis-and-treatment department terminal 11 to send an order for a report. The report producing terminal 13 receives the order from the diagnosis-and-treatment department terminal 11 through the order reception terminal in the inspection department 12.

The interpreting doctor checks the order on the report producing terminal 13, and starts making the report 18 requested. When the report editor screen 47 appears on the display 37b, the image display screen 46 synchronously appears on the display 37a.

Figure 8:
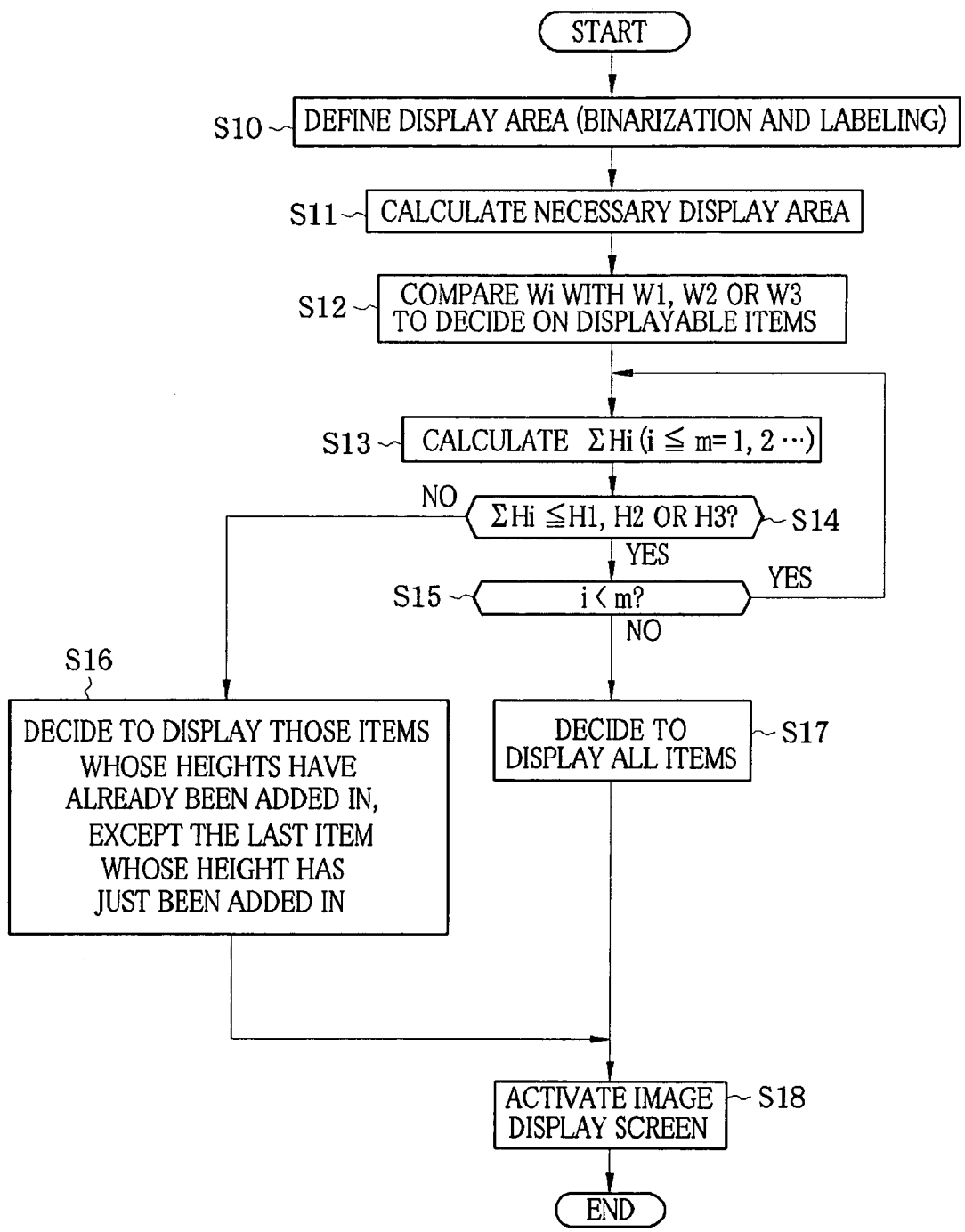
FIG. 8 is a flowchart illustrating a sequence of processes for displaying an image display screen.

At a first step S10 as shown in FIG. 8, the area defining section 42 defines the display areas 60 and 61 before the image display screen 46 appears. The area defining section 42 first receives the data of the medical image 17 from the database access section 41 and binarizes it to produce a monochrome image. Next, the monochrome image is subjected to the labeling process, to extract a main part of a subject contained in the medical image 17, i.e. the main subject display area 60.

After extracting the main subject display area 60, the area defining section 42 determines the respective sections 62 to 64 of the accessory information display area 61. Then, the area defining section 42 outputs information on the respective sizes of the sections 62 to 64 of the accessory information display area 61 to the console controller 40 and the display style deciding section 43.

At a second step S11, the display style deciding section 43 calculates a necessary display area of each individual item of the accessory information, and temporarily stores information on the respective sizes of the calculated necessary display areas in the memory 31 in the form of a data table allocating them to the respective items.

At a step S12, the display style deciding section 43 compares the width Wi of the necessary display area of each individual information item with the width W1, W2 or W3 of the assigned display section 62, 63 or 64. Thereby, those items having the width Wi of not more than the width W1, W2 or W3 of the assigned section 62, 63 or 64 are determined to be displayable in the assigned section (Wi≤W1, W2 or W3). On the contrary, the display style deciding section 43 decides against displaying those items having the width Wi of more than the width W1, W2 or W3 (Wi>W1, W2 or W3).

At a step S13, the heights Hi of the respective necessary display areas of those items which are decided to be displayable at the step S12 are seriatim added up in order of most important first, to calculate the sum ΣHi. Each after adding the height Hi of the necessary display area of one item, the sum ΣHi is compared with the height H1, H2 or H3 of the applicable section 62, 63 or 64, the heights H1 to H3 being determined by the area defining section 42. The process of the step S13 is repeated for one item after another so far as the sum ΣHi is not more than the height H1, H2 or H3 ("Yes" at a step S14) and the display style deciding section 43 has not yet added in the height hm of the necessary display area for the least important item among ones applied to the same display section.

If the sum ΣHi gets over the height H1, H2 or H3 before the height hm for the least important item is added in ("No" at a step S14), the display style deciding section 43 decides not to display the item whose height Hi has just been added in and the following less important items (step S16), but to display merely those items of higher degrees of importance among ones assigned to the same display section 62, 63 or 64. On the other hand, if the sum ΣHi is not more than the height H1, H2 or H3 after the height hm of the last and least important item is added in ("Yes" at the step S14, and "No" at the step 15), the display style deciding section 43 decides to display all of the items in the assigned display section 62, 63 or 64 (step S17). The display style of the accessory information items is output from the display style deciding section 43 to the console controller 40.

In accordance with the commands from the area defining section 42 and the display style deciding section 43, the console controller 40 controls the display style of the display areas 60 and 61 as it activates the image display screen 46 (step S18).

The interpreting doctor writes a finding in one finding entry box 48 on the report editor screen 47 while observing the medical image 17 on the image display screen 46. When the data of the finding enters, the console controller 40 forwards it to the editorial processor 44.

The editorial processor 44 sorts the finding data into a block for each finding entry box 48, attaches the finding ID to each block of the finding data, and records the data of the respective finding in the data of the report 18. Besides the finding data, the inspection ID, the patient ID, the name of patient, the doctor ID, and the data of the annotation 65 are attached to the data of the report 18.

The interpreting doctor instructs an end of making the report 18 after inputting the finding. Upon the instruction to end the report making, a request for storing data of the report 18 is sent from the database access section 41 of the report producing terminal 13 to the database server 14. Upon receipt of the request for data-storage from the report producing terminal 13, the storage processor 50 of the database server 14 executes a process of storing the data of the report 18, thereby completing a report making process for one report 18.

After completing making the report 18, the report producing terminal 13 sends a notice of completion of the report 18 to the requester's diagnosis-and-treatment terminal 11. The requesting doctor makes an access to the report database 21 through the diagnosis-and-treatment department terminal 11, to read out the report 18 from the address in the report database 21, which is included in the notice of completion. Then the display device 37 of the diagnosis-and-treatment department terminal 11 outputs a report display screen for displaying the report 18 and an image display screen for displaying the medical image 17 relating to the report 18. So the requesting doctor views these screens to read and check the contents of the report 18.

As described so far, the display style of the accessory information items is decided taking account of their respective necessary display areas and importance degrees. Therefore, relevant items will be displayed prior to less important items, while maintaining the image quality of the medical image 17. Accordingly, the process of making the report 18 is smoothed, and the danger of medical errors will be reduced.

Since the area defining section 42 automatically extracts the main subject display area 60 and determines the accessory information display area 61, the interpreting doctors are saved from the labor of defining the respective display areas 60 and 61.

In the above-described embodiment, a number of tomograms relating to one inspection are subjected to the binarization and labeling processes to extract a main subject portion from each individual tomogram, and the largest one of the extracted main subject portions is determined to be the main subject display area 60. It is, however, possible to extract main subject display areas from the respective tomograms. In a case where the main subject display area 60 is fixed in size, like when the medical image 17 is an endoscopic image or an ultrasonic image, the area defining section 42 is unnecessary. Moreover, the binarization process may be replaced with a gray-scaling process.

In the above-described embodiment, the heights Hi of the necessary display areas are added up in the order from the most important item, and every time the height Hi is newly added in, the sum ΣHi is compared with the height H1, H2 or H3 of the corresponding display section 62, 63 or 64, to discriminate between those items to be displayed in the accessory information display area 61 and those to be omitted from the accessory information display area 61. However, the present invention is not to be limited to this embodiment. It is alternatively possible to calculate the sum ΣHi of all items assigned to the same display section, and then subtract the height Hi for one item from the sum ΣHi in order of least important item first. After every subtraction of the height Hi, the sum ΣHi shall be compared with the height H1, H2 or H3 of the applied display section. If the height Hi of the necessary display area is constant to every item, it is also possible to compare an integral multiple of the height Hi with the height H1, H2 or H3.

Although the above-described embodiment decides against displaying those items which need a display area beyond the display section 62, 63 or 64, the present invention is not limited to this embodiment. The following description relates to other embodiments of the present invention, wherein those components which are designated by the same reference numerals as used in the first embodiment have the same structure and operation, so that the detail of these components will be omitted.

Second Embodiment

Figure 9:
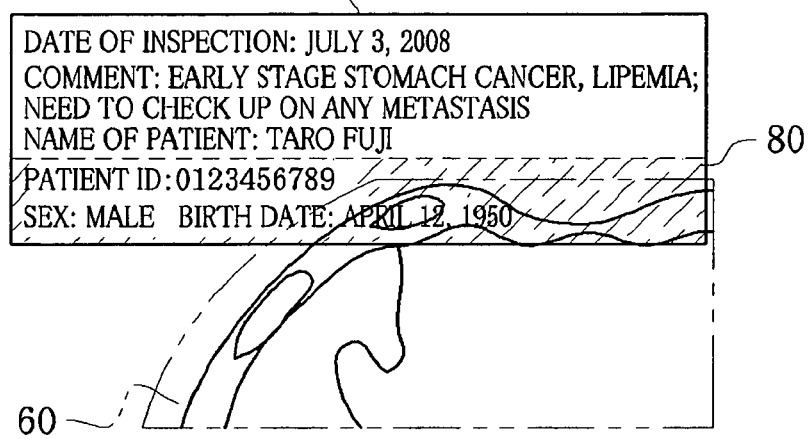
FIG. 9 is a diagram illustrating an example of an image display screen provided with a transparent display frame according to a second embodiment of the present invention.

In the second embodiment shown in FIG. 9, an image display screen 46 is provided with a transparent display frame 80, which is illustrated as an area hatched by chain-dotted lines. The transparent display frame 80 is an extension from the bottom of a first section 62 of an accessory information display area, whose size and position are defined by an area defining section 42. So the transparent display frame 80 overlaps an upper fragment of a main subject display area 60. The transparent display frame 80 is for example displaying those items which are decided to be omitted from the first section 62 as a result of the above-described calculation and comparison of the sum ΣHi with the height H1 of the first section 62. The items are displayed transparently in the transparent display frame 80, so that they will not hinder the visibility of the main subject display area 60. A console controller 40 controls the degree of transparency of the displayed items in the transparent display frame 80.

FIG. 9 shows an example where the items "patient ID" and "sex and birth date of patient" are decided to be displayed in the transparent display frame 80; the items "date of inspection", "comment", and "name of patient" are displayed substantially at a normal display density (opaque), like in the above-described embodiment, whereas the items "patient ID" and "sex and birth date of patient" are displayed transparently at a lower density than the normal density.

Even though the transparent display frame 80 is transparent, the more the transparent display frame 80 invades the main subject display area 60, the visibility of the main subject display area 60 gets worse. Therefore, it is preferable to give an upper limit to the overlapping portion between the transparent display frame 80 and the main subject display area 60, i.e. to the height of the transparent display frame 80. In that case, if the total height of the necessary display areas of those items which are to be displayed in the transparent display frame 80 is above the upper limit of the height of the transparent display frame 80, some of these items shall not be displayed.

It is also possible to change the transparency of the items according to their importance. For example, relevant items will be displayed at a lower transparency to make them more substantial, and less relevant items will be displayed at a high transparency to make them fainter. Moreover, it is possible to display merely those items transparently which overlap the main subject display area 60, e.g. latter half of the item "sex and birth date of patient" in FIG. 9, while displaying such an item that does not overlap the main subject display area 60, e.g. "patient ID" in FIG. 9, substantially in the transparent display frame 80.

Furthermore, it is possible to provide a regular display frame and an irregular display frame in an accessory information display area, the regular display frame displaying the accessory information in a regular style, wherein the whole content of each information item is displayed constantly with a regular font size, like the display style of the first embodiment. On the other hand, the irregular display frame displays the accessory information in an irregular style that differs from the regular display style. The following embodiments show variations of the irregular display frame.

Third Embodiment

According to the third embodiment shown in FIG. 10, a first display section 62 is provided with a scroll display frame 81. The scroll display frame 81 displays those items which are decided not to be displayed in the regular style. The decision about which item is to be displayed in the regular style may be made through the same processes as described with respect to the first embodiment: comparison between the width Wi of the necessary display area of each item and the width W1, W2 or W3 of an applied display section 62, 63 or 64, as well as comparison between the sum ΣHi of the heights Hi of the necessary display areas and the height H1, H2 or H3 of the applied display section. Then, those items which are refused from being displayed in the regular style are displayed in the scroll display frame 81, being scrolled continuously in a horizontal direction. Under the control of a console controller 40, the scrolling speed of the scroll display frame 81 is set at such a level that allows the interpreting doctor to read the displayed items with ease.

FIG. 10 shows an example where the width Wi of the necessary display area of the item "comment" is greater than the width W1 of the first section 62, and the items "patient ID" and "sex and birth date" are excluded from ones to be displayed regularly as the result of comparison between the sum ΣHi and the height H1. The scroll display frame 81 is partitioned into two rows: one for displaying the item "comment", and the other for displaying the items "patient ID" and "sex and birth date" successively. In this example, the item "date of inspection" alone is displayed in the regular style.

Figure 10A:
FIG. 10 is a diagram illustrating an example of an image display screen provided with a scroll display frame according to a third embodiment of the present invention.
Figure 10B:
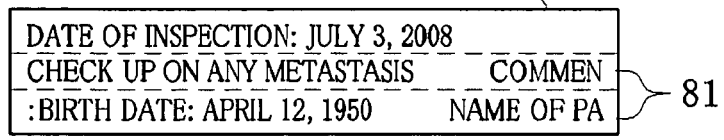

FIG. 10A shows an initial condition of the scroll display frame 81, displaying the former halves of the item "comment" and the items "patient ID" and "sex and birth date". FIG. 10B shows a condition scrolled with time, displaying the latter half and the head of the "comment", and the latter half of the "sex and birth date" and the head of the "patient ID".

The scrolling speed may vary according to the importance of the item, like transparency in the second embodiment. For example, a low scrolling speed is applied to the item with higher importance and a higher scrolling speed to the item with lower importance. It is also possible to freeze the transparent display frame 80 in response to a command from an input device 38. For an item that is given a higher grade of importance, like the item "comment", it is possible to wrap the line at the end of the accessory information display area to display the whole sentence of this item in multiple lines, instead of scrolling it.

Fourth Embodiment

According to the fourth embodiment shown in FIG. 11, a first display section 62 is provided with a switchable display frame 82. The switching display frame 82 displays such items that are decided not to be displayed in the regular style, for example, as a result of comparison between the sum ΣHi and the height H1, H2 or H3 of the applied display section. A console controller 40 controls the switching speed of the switching display frame 82 so that the interpreting doctor can read the displayed items with ease. The console controller 40 switches over the items displayed in the switching display frame 82 upon receipt of a switching command from an input device 38.

FIG. 11 shows a case where the items "patient ID" and "sex and birth date" are sorted out as being unsuitable for the regular display style. The switching display frame 82 is located in a lower portion of the section 62. As shown in FIG. 11A, the item "name of patient" is displayed initially in the switching display frame 82, as it is graded the highest among the items "name of patient", "patient ID", and "sex and birth date". FIG. 11B shows a second display condition of the first section 62 a certain time after the initial, or when a switching command is given through the input device 38. In the second display condition, the switching display frame 82 is switched from the item "name of patient" to the item "patient ID", the importance grade of which is next to that of the item "name of patient". In a given time or upon another switching command from the input device 38, the switching display frame 82 switches from the second condition to a third condition as shown in FIG. 11C, wherein the item "sex and birth date of patient" is displayed in place of the item "patient ID".

The switching speed may vary according to the importance of the item, like transparency or scrolling speed in the second or third embodiment. For example, a low switching speed is applied to the item of higher degree of importance and a high switching speed to the item of lower degree of importance. Concerning such an item that needs a greater width Wi than the width W1, W2 or W3 of the display section 62, 63 or 64, like the item "comment" in the second embodiment, it is possible to divide its character string into sequential segments of appropriate lengths, and display the segments one after another in the switching display frame 82. It is also possible to freeze the switching display frame 82 in response to a command from an input device 38.

Fifth Embodiment

According to the fifth embodiment shown in FIG. 12, a first display section 62 is provided with a small font display frame 83 for displaying the accessory information with a smaller font size than the regular font size. The small font display frame 83 displays those items which are decided to be hard to display in the regular style, for example, as a result of comparison between the sum ΣHi and the height H1, H2 or H3 of the applied display section. A console controller 40 controls the font of the small font display frame 83 to a predetermined size.

FIG. 12 shows an example where the items "patient ID" and "sex and birth date" are determined to be incapable of being displayed in the regular style. In this case, merely the items "date of inspection" and "comment" are displayed with the regular font size in the section 62. The small font display frame 83 is located below the items of the regular font size and displays the items "name of patient", "patient ID", and "sex and birth date" with the small font size, e.g. one third of the regular font size.

It is possible to put more variation in font size with the importance of the items, like transparency or scrolling speed or switching speed in the second, third or fourth embodiment. For example, a larger font is applied to the item of higher degree of importance and a smaller font to the item of lower degree of importance. If the font size of the small font display frame 83 would be too small in order to arrange the items in parallel to each other, like as shown in FIG. 12, it is possible to arrange the items in serial in the small font display frame 83. If the length of the character strings of the serially arranged items is greater than the width W1 of the section 62, it is possible to scroll the items in the small font display frame 83, like as described in the third embodiment.

In the first embodiment, even a relevant item is decided against being displayed, if the width Wi of the necessary display area of that item is over the width W1, W2 or W3 of the display section 62, 63 or 64. Moreover, because of the limit in height H1, H2 or H3 of the display section 62, 63 or 64, less important items are more likely to be omitted.

On the contrary, according to the second to fifth embodiments, those items which would be refused from being displayed in the first embodiment will be displayed in the manner as set forth above: transparently, scrolled, switched, or with a smaller front size. So it becomes possible to display more accessory information, which is useful for the interpreting doctor to make the report 18. Since the second to fifth embodiment display the items of relatively high importance in the regular style, it is easy for the viewer to discriminate relevant information items from less relevant ones.

Although the second to fifth embodiments have been described in relation to the first display section 62, the same applies to other display sections 63 and 64 of the accessory information display area 61. Moreover, the second to fifth embodiments have been described as a relief measure for those information items which the first embodiment would decide not to display, to display as many items as possible, but the present invention is not limited to these configurations. The second to fifth embodiment are applicable to a case where a decision as to whether to display an information item is made depending upon its importance alone, and every item whose grade of importance is not less than a predetermined threshold level, e.g. 10, is decided to be displayed.

In that case, a display style deciding section 43 decides not to display those items whose grade of importance is less than the predetermined threshold level, and decides to display those items whose grades of importance are higher than the threshold level. These items may be displayed in the scrolled style, or switched from one another, or with a small font size, or transparently. For instance, provided that there are three items as the subjects of the scrolling display, all of these items will be displayed in the scrolled style in the second embodiment. On the other hand, in the case where the threshold level is adopted, if the items to be displayed in the scrolled style include one whose grade of importance is less than the threshold level, this item is not displayed, but other two items are displayed in the scrolled style.

Figure 13A:
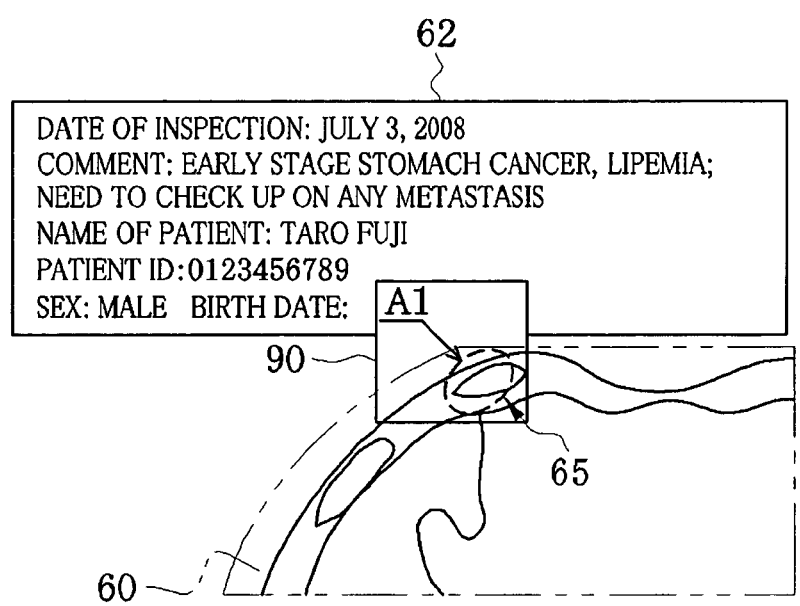
FIG. 13A shows an example of an image display screen wherein an annotation display area is superposed on an accessory information display area.

Although the above-described embodiments decide the display style of the accessory information that is already attached to the medical image 17 before the report 18 is produced, the same method can be applied to deciding the display style of such information as attached to the medical image 17 while the report 18 is being produced, like annotations 65. Because a display area 90 of an annotation 65 can sometimes overlap with an accessory information display area 61, like as shown in FIG. 13, the sixth embodiment as set forth below is suggested as a solution for this case.

Sixth Embodiment

Figure 13B:
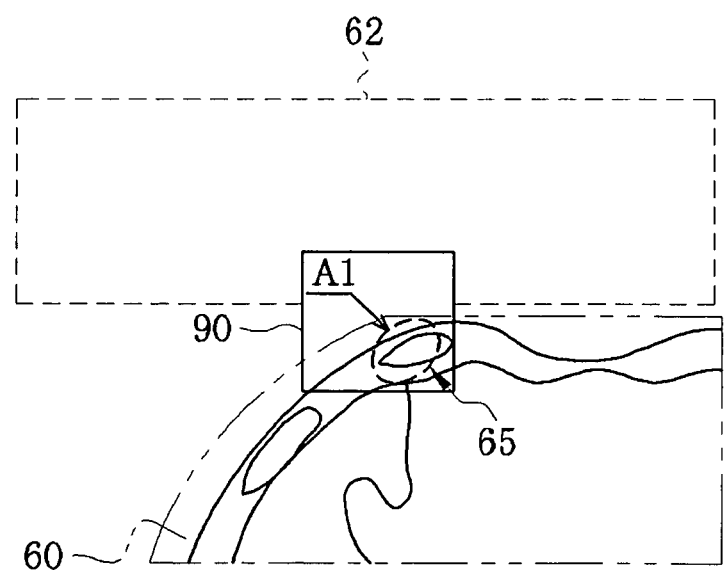
FIG. 13B shows another example wherein only the annotation display area is displayed while the accessory information display area is made invisible.
Figure 14:
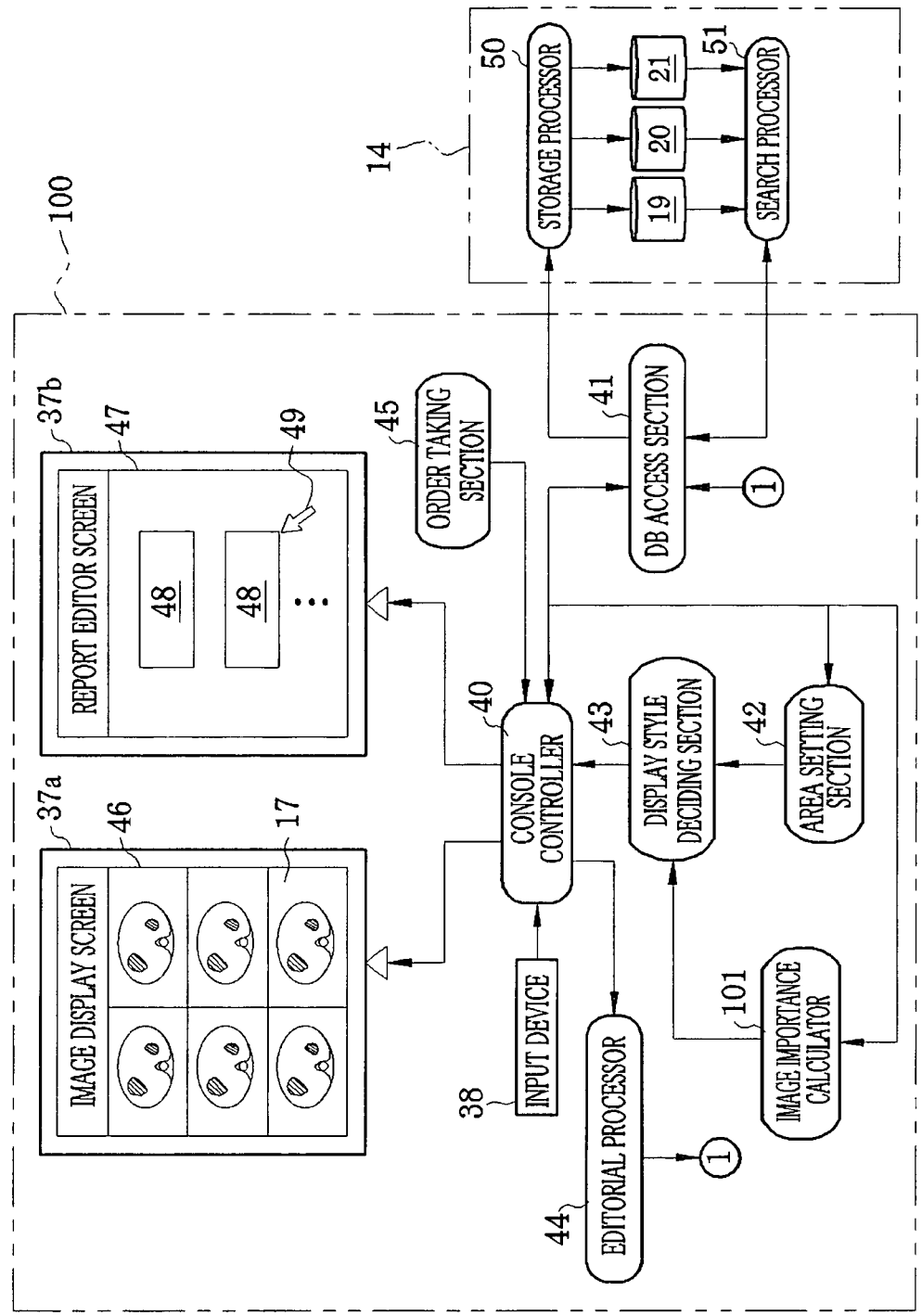
FIG. 14 is a diagram illustrating schematic configurations of a report producing terminal and a database server, according to a seventh embodiment of the present invention.

In the sixth embodiment, the accessory information display area 61 and the annotation display area 90 are treated as separate layers. For example, where the layer for the annotation display area 90 is set to be an upper layer over the layer for the accessory information display area 61, a console controller 40 lays the annotation display area 90 over the accessory information display area 61, i.e. a first section 62 in the example shown in FIG. 13A, so that the accessory information display area 61 is partly hidden behind the annotation display area 90. Alternatively, as shown in FIG. 13B, it is possible to extinguish the accessory information display area 61 and display merely the annotation display area 90.

It is possible to make the upper layer switchable between the display areas 61 and 90 by operating an input device 38. When the layer for the accessory information display area 61 is set to be the upper layer over the layer for the annotation display area 90, the accessory information display area 61 (the first section 62) is laid over the annotation display area 90 in opposition to the example of FIG. 13A, or only the accessory information display area 61 is displayed and the annotation display area 90 is made invisible in opposition to the example of FIG. 13B. Thus, separating the respective display areas 61 and 90 into different layers will solve the problem that the overlap between the display areas 61 and 90 worsens their visibility.

Although the above-described embodiments decide the display style of the accessory information while taking account of the importance degrees of the respective information items, it is possible to calculate degrees of importance of respective regions of the medical image 17 and take the importance degrees of the medical image regions as well as the information items into consideration to decide the display style of the accessory information.

Seventh Embodiment

In a report producing terminal 100 of the seventh embodiment as shown in FIG. 17, a CPU is provided with an image importance calculator 101 in addition to the same components as the CPU 30 of the report producing terminal 13 of FIG. 3, a console controller 40, a DB access section 41, an area defining section 42, a display style deciding section 43, an editorial process section 44, and an order taking section 45. The image importance calculator 101 receives data of a medical image 17 from the database access section 41, extracts a region of interest inside the medical image 17, and calculates degrees of importance of respective regions of the medical image 17.

As a known method of extracting a region of interest, there is a method of detecting a lesion or the like through pattern recognition and regarding it as the region of interest. For the pattern recognition, face discrimination techniques as used in digital cameras, such as those disclosed in JPA Nos. 2005-284203, 2005-286940 and 2005-156967, are applicable. Concretely, such patterns that are specific to some lesions or the like are prepared as templates, and each area (search area) of the medical image 17 is individually checked about similarly in shape and color to the respective templates. While varying the size and angle of the search areas, the whole area of the medical image 17 is checked up to extract the most similar portion to one template as a region of interest.

If the medical image 17 is an endoscopic image, it is possible to process the medical image 17 to enhance blood vessels in the medical image 17, and detect a blood vessel concentrating portion as a region of interest. The blood vessel enhancing process is well known, for example, disclosed in JPA 2003-93342. The image importance calculator 101 generates a differential signal by differentiating a color signal, e.g. a green signal, other than a red signal as a main color signal of the blood vessel. The image importance calculator 101 amplifies the differential signal, and then amplifies the red signal on the basis of the amplified differential signal, thereby enhancing the blood vessels. Because the blood vessel concentrating portion shows a higher density of red, a region of the highest density of red can be extracted as the region of interest from the medical image 17.

After extracting the region of interest (ROI) in the manner as above, the image importance calculator 101 gives the top grade of importance, e.g. 100 point, to the region of interest. Then, the image importance calculator 101 calculates importance degrees of respective regions inside the medical image 17, for example, according to the distance from a center pixel of the region of interest.

Figure 15:
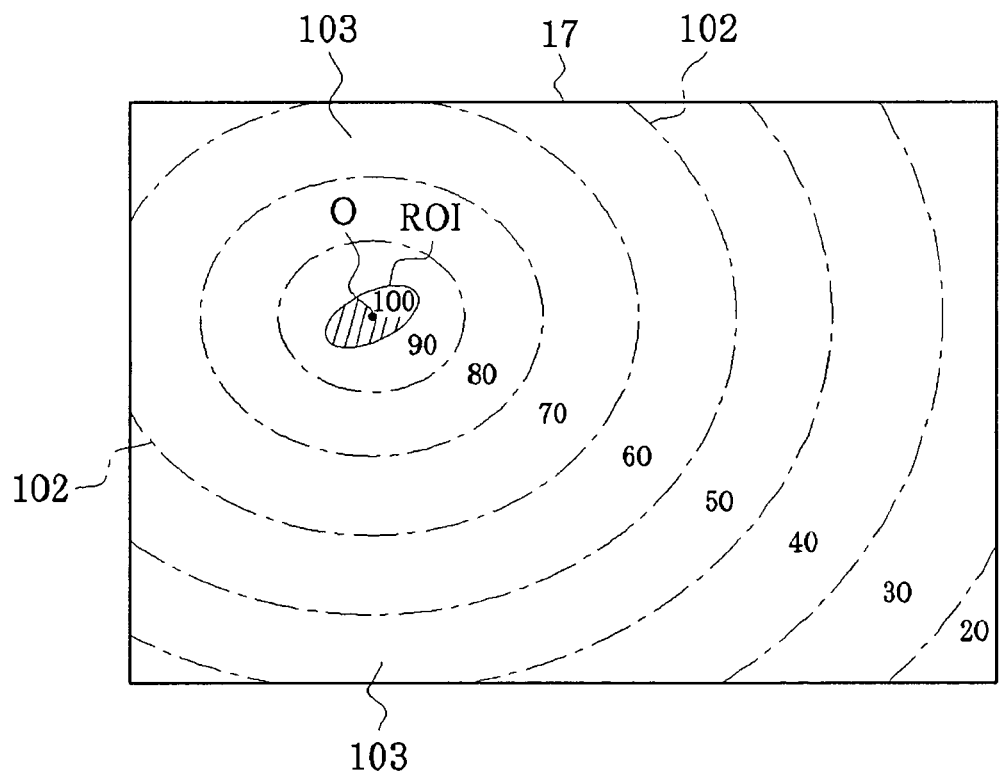
FIG. 15 is an explanatory diagram illustrating importance degrees of peripheral regions around a region of interest in a medical image.

Concretely, as shown schematically in FIG. 15, several concentric ellipsoids 102 are hypothetically drawn around the center pixel O of the region of interest ROI on the medical image 17 to partition the whole area of the medical image 17 with the ellipsoidal lines 102 into concentric regions 103.

Note that the ellipsoidal lines 102 may be replaced with circular or rectangular lines. Just like a dart board, different scores of importance are allotted to the respective regions 103, with 10-point decrements in between in the order from nearest to the center point 0, i.e. 100, 90, 80 . . . . It is alternatively possible to score the importance according to other factor than the distance from the center pixel O, such as similarity in image characteristic value to the region of interest ROI. The image importance calculator 101 outputs information on the calculated scores of importance to a display style deciding section 43.

The display style deciding section 43 decides the display style of an accessory information display area by the importance degrees of the respective regions 103 of the medical image 17, strictly a main subject display area 60 of the medical image 17, as well as the importance degrees of the respective items of the accessory information. If there is any such accessory information item that cannot fit in the accessory information display area 61, the display style deciding section 43 compares the importance degree of this item with the importance degree of an appropriate one of the regions 103 of the medical image 17, in order to decide whether this region 103 is available for displaying the information item that does not fit into the accessory information display area 61.

If the importance of this accessory information item is greater than the importance of the compared region 103 of the medical image 17, a transparent display frame 80 is provided as an extension of the for this item to display it transparently in the region 103, like the fifth embodiment, or the information item is superimposed as an upper layer on the image region 103, like the sixth embodiment. On the contrary, if the importance of this accessory information item is less than the importance of the region 103, the display style deciding section 43 decides not to display this information item.

Consequently, if the region 103 of the medical image 17 is relatively important, it will not be hidden unexpectedly behind the accessory information. If the region 103 is less important than the accessory information, the accessory information will be displayed at the price of this region 103.

Although the region of interest ROI is automatically extracted by the image importance calculator 101 in the above-described embodiment, it is possible that the interpreting doctor designates the region of interest through an input device 38. For example, if an annotation 65 is allocated to a portion of the medical image 17, the portion with the annotation 65 may be held as a region of interest ROI. Moreover, the importance of the medical image 17 may be graded manually by the interpreting doctor or the like. Although the above-described embodiment calculates the importance degrees of the respective regions of the whole area of the medical image 17, it is sufficient to calculate the importance degree of one region 103 of the medical image 17, which shall be taken over for displaying the accessory information item that cannot fit in the accessory information display area.

If the accessory information display area 61 is capable of displaying all items of the accessory information, these items may be arranged at random regardless of their importance unlike the illustrated embodiments. Although the above-described embodiments regard the sections 62 to 64 of the accessory information display area 61 as dependent sections and decide the display style of each section individually, it is possible to decide the display style regarding these sections as a united display area. Namely, information items are not previously allocated between these sections. For instance, they are arranged sequentially in the first, second and third section in the order from the highest importance. In that case, the transparent display frame 80 as mentioned in the second embodiment or the irregular display frame as mentioned in the third, fourth or fifth embodiment will be disposed mostly in the third section 64. Moreover, if the extracted main subject display area 60 is too big to provide a suitable room for the accessory information display area 61, it can't be helped reducing the size of the medical image 17.

In the above embodiments, the display style of the accessory information display area is decided on producing the report on the report producing terminal. But it is possible to decide the display style of the accessory information display area when the medical image is viewed along with the produced report on the diagnosis-and-treatment terminal. In this case, information on the display style of the accessory information display area may be recorded in the data of the medical image after it is decided by the display style deciding section of the report producing terminal. Then it becomes possible to display the medical image on the diagnosis-and-treatment department terminal in the same display style as on the image display screen of the report producing terminal. It is of course possible to provide the diagnosis-and-treatment department terminal with the components 40 to 43 of FIG. 3, to serve the diagnosis-and-treatment terminal for the medical image display apparatus of the present invention.

Furthermore, the medical image display apparatus of the present invention may be configured such that the interpreting doctor can choose between the above-described display styles. Then the interpreting doctor chooses a suitable display style according to the doctor's preference or intention or purpose of the report. It is also possible to apply some of the above-mentioned display styles compositely to one report. For example, the display styles of the third and fifth embodiments may be joined together such that the font of less important items is sized down and such items that need a greater width (line length) than the width (horizontal length) of the accessory information display area are scrolled. Alternatively, the display styles of the fourth and fifth embodiments may be joined together such that the font of less important items is sized down and displayed by turns. This configuration will reduce the requisite height of the scroll display frame or switching display frame, improving the efficiency of displaying the accessory information.

Although the above embodiments have been described with reference to some inspections carried out in the inspection department 12, the kind of inspection is not limited to the referred examples, but may be PET (Positron Emission Tomography), ultrasonography, endoscopy and so forth.

Although the medical image display apparatus of the present invention has been described as one with a single report producing terminal in the above embodiments, more than one report producing terminal may constitute the apparatus of the present invention. Although the importance table is stored in the storage device of the report producing terminal, the importance table may be stored in the database server. In that case, the database access section of the report producing terminal sends the database server a search request for the importance table and receives the search result.

In a client-server type information system that consists of clients (report reproducing terminals) and a server (database server) like the above embodiment, the client program for report-editing may be a specific program or a general-purpose browser that complies with the WWW (World Wide Web) protocol such as HTTP (Hyper Text Transfer Protocol).

With the specific program, the report editor screen is produced on the basis of screen data defined by the specific program. With the general-purpose browser, data of a report editing screen is stored for example in a Web server, so that the clients access the Web server to download the data of the report editor screen that is processed into a Web page format. The browser of the client decodes the source code of the received Web page and produces the report editing screen. The Web server may double as the database server 14, or may be a different server. With the general-purpose browser, a CPU of the Web server constitutes the console controller and the editor processor by itself or in cooperation with a CPU of the client.

The data storage device that constitutes the database is not limited to the data server, but may be a storage device that is connected through a network, such as NAS (Network Attached Storage) or SAN (Storage Area Network). Thus, physical structures of the computer systems may be modified appropriately.

Although the above embodiments refer to LAN as the network, it is possible to use LAN and WAN (Wide Area Network) as a combined network in a medical facility where diagnosis-and-treatment departments and inspection departments are dispersed in several centers.

As will be obvious from the above embodiments, the scope of the present invention expands to the form of a program and a storage medium storing this program.

Thus, the present invention is not to be limited to the above embodiments but, on the contrary, various modifications will be possible without departing from the scope of claims appended hereto.

What is claimed is:

1. A medical image display apparatus comprising:
a display controller for displaying a medical image and appendant information about said medical image overlapped with each other on a display screen, said appendant information consisting of a plurality of items;
a storage device for storing respective grades of importance attached to said appendant information items; and
a display style deciding device for deciding how to display said appendant information in an appendant information display area that is provided outside a main subject display area of said medical image, wherein said display style deciding device decides priority in arranging said appendant information items in the order of most important first,
wherein said display style deciding device compares the size of a necessary area for displaying said appendant information items in a regular style with the size of said appendant information display area, to discriminate between those appendant information items which fit in said appendant information display area and those which do not fit in said appendant information display area.

2. A medical image display apparatus as recited in claim 1, further comprising an area defining device that analyzes said medical image to extract said main subject display area, and defines said appendant information display area outside said extracted main subject display area.

3. A medical image display apparatus as recited in claim 1, wherein said display style deciding device decides not to display those appendant information items in said appendant information display area, which do not fit in said appendant information display area.

4. A medical image display apparatus as recited in claim 1, wherein said display style deciding device sets up a transparent display frame in said main subject display area, said transparent display frame displaying those appendant information items which do not fit in said appendant information display area, transparently at a lower density than a regular display density in said appendant information display area.

5. A medical image display apparatus as recited in claim 4, wherein said display style deciding device compares the grade of importance of each of those appendant information items which do not fit in said appendant information display area with a predetermined threshold value, to discriminate between those appendant information items which are to be displayed in said transparent display frame and those which are not to be displayed in said transparent display frame.

6. A medical image display apparatus as recited in claim 4, wherein said display controller changes transparency of said transparent display frame according to the grade of importance of the appendant information item displayed therein.

7. A medical image display apparatus as recited in claim 6, wherein said display style deciding device sets up a regular display frame for displaying said appendant information in the regular style and an irregular display frame for displaying said appendant information in an irregular style different from the regular style within said appendant information display area, and said display style deciding device decides to arrange those appendant information items which are given higher grades of importance preferentially in said regular display frame.

8. A medical image display apparatus as recited in claim 7, wherein said display style deciding device decides all of those information items which cannot be displayed in said regular display frame to be displayed in said irregular display frame.

9. A medical image display apparatus as recited in claim 7, wherein said display style deciding device compares the grade of importance of each of those appendant information items which cannot be displayed in said regular display frame with a predetermined threshold value, to discriminate between those appendant information items which are to be displayed in said irregular display frame and those which are not to be displayed in said irregular display frame.

10. A medical image display apparatus as recited in claim 7, wherein said regular display frame is for displaying said appendant information constantly as a whole in a regular size.

11. A medical image display apparatus as recited in claim 7, wherein said irregular display frame includes a scroll display frame for displaying said appendant information item in a scrolling fashion.

12. A medical image display apparatus as recited in claim 11, wherein said display controller changes the speed of scrolling in accordance with the importance of each individual appendant information item displayed in said scroll display frame.

13. A medical image display apparatus as recited in claim 7, wherein said irregular display frame includes a switching display frame for displaying a plurality of said appendant information items by turns.

14. A medical image display apparatus as recited in claim 13, wherein said display controller changes speed of switching between said appendant information items with the importance of each individual appendant information item.

15. A medical image display apparatus as recited in claim 7, wherein said irregular display frame includes a small font display frame for displaying said appendant information item with a smaller font size than a font size in said regular display frame.

16. A medical image display apparatus as recited in claim 15, wherein said display controller changes the font size of said appendant information item with the importance of each individual appendant information item.

17. A medical image display apparatus as recited in claim 1, wherein said appendant information display area includes a first display area for displaying those appendant information items which are previously attached to said medical image before being displayed on said display screen, and a second display area for displaying such appendant information that is attached to said medical image after being displayed on said display screen, and said display controller treats said first and second display areas as separate layers, such that one of said first and second display areas is set to be an upper layer and superposed on the other display area of a lower layer so as to hide the display area of the lower layer behind the display area of the upper layer, or such that only one of said first and second display areas is displayed on said display screen without the other display area being displayed.

18. A medical image display apparatus as recited in claim 17, wherein the appendant information attached to said medical image after being displayed on said display screen includes an annotation assigned to a region of interest inside said medical image.

19. A medical image display apparatus as recited in claim 1, wherein said display style deciding device decides whether or not to display an appendant information item that will overlap with a region of said medical image by comparing importance between said region of said medical image and said appendant information item.

20. A medical image display apparatus as recited in claim 19, further comprising an importance calculator that analyzes said medical image to grade the importance of respective regions of said medical image.

21. A medical image display method for displaying a medical image and appendant information about said medical image overlapped with each other on a display screen of a medical image display apparatus, said appendant information consisting of a plurality of items, said method comprising steps of:
storing an importance table grading importance of respective items of said appendant information in a storage device of said medical image display apparatus;
with use of a display style deciding device of said medical image display apparatus, deciding a display style of said appendant information in an appendant information display area that is provided outside a main subject display area of said display screen, such that said appendant information items are displayed in the order of most important first based on said importance table; and
with use of a display controller of said medical image display apparatus, controlling displaying said medical image and said appendant information according to the decided display style,
wherein said display style deciding step comprises a step of deciding with use of said display style deciding device how to deal with those appendant information items which cannot be displayed in a regular style in said appendant information display area.

22. A non-transitory computer-readable medium comprising a program for controlling a computer to perform a medical image display process for displaying a medical image and appendant information about said medical image overlapped with each other on a display screen of said computer, said medical image display process comprising steps of:
with use of a display style deciding device of said computer, deciding a display style of said appendant information in an appendant information display area that is provided outside a main subject display area of said display screen, such that said appendant information items are displayed in the order of most important first; and
with use of a display controller of said computer, controlling displaying said medical image and said appendant information according to the decided display style wherein said display style deciding step comprises a step of deciding with use of said display style deciding device how to deal with those appendant information items which cannot be displayed in a regular style in said appendant information display area.

\* \* \* \* \*